United States Patent [19]
Pytel et al.

[11] Patent Number: 5,195,522
[45] Date of Patent: Mar. 23, 1993

[54] TONOMETRY SENSOR CALIBRATION APPARATUS

[75] Inventors: Kenneth J. Pytel, San Diego; Stephen A. Martin, Carlsbad; Robert D. Butterfield, Poway, all of Calif.

[73] Assignee: IVAC Corporation, San Diego, Calif.

[21] Appl. No.: 717,224

[22] Filed: Jun. 18, 1991

Related U.S. Application Data

[63] Continuation-in-part of Ser. No. 621,165, Nov. 30, 1990, Pat. No. 5,158,091.

[51] Int. Cl.⁵ ............................................. A61B 5/02
[52] U.S. Cl. ..................................... 128/680; 128/748; 128/774; 128/690; 73/1 B
[58] Field of Search ............... 128/748, 774, 687, 688, 128/689, 690; 73/4 V, 1 B

[56] References Cited

U.S. PATENT DOCUMENTS

| | | | |
|---|---|---|---|
| 3,219,035 | 11/1965 | Pressman et al. | |
| 3,842,357 | 10/1974 | Hutchins | |
| 4,572,204 | 2/1986 | Stephens | 128/748 |
| 4,658,829 | 4/1987 | Wallace | 128/748 |
| 4,901,733 | 2/1990 | Kaida et al. | 128/690 |

*Primary Examiner*—Lee S. Cohen
*Assistant Examiner*—Brian Casler

[57] ABSTRACT

A calibration apparatus for use in calibrating a tissue stress sensor used in a blood pressure monitoring system. The calibration apparatus includes a calibration head which is adapted to be retained in close proximity to a tissue stress sensor. The calibration head includes means for heating the tissue stress sensor. A calibration system is also disclosed for calibrating a blood pressure monitoring system, the blood pressure monitoring system employing a stress sensor for generating an electric output signal representative of tissue stress data. The calibration system comprises a tissue stress sensor having a displaceable diaphragm and a sealed chamber. The chamber has a continuous wall defining an inner volume and an outer volume. The displaceable diaphragm comprises a portion of the continuous wall, whereby the displaceable diaphragm is responsive to a pressure differential between the inner chamber volume and the outer chamber volume. The vacuum means is fluidly coupled to the inner volume of the sealed chamber for applying a controlled vacuum to the inner volume of the chamber whereby the diaphragm is displaced in response to the application of the vacuum. Calibration means is provided for detecting the sensors response to heating and displacing of the sensor diaphragm and for generating corrective data for use in correcting the effects of sensor temperture on the data generated by the sensor.

26 Claims, 2 Drawing Sheets

TONOMETRY SENSOR CALIBRATION APPARATUS

RELATED APPLICATION

This application is a continuation-in-part of U.S. application Ser. No. 07/621,165 filed Nov. 30, 1990, U.S. Pat. No. 5,158,091.

TECHNICAL FIELD

The present invention generally relates to calibration systems, snd more particularly relates to a and apparatus for calibrating a system for noninvasively determining the intra-arterial blood pressure of a wearer.

BACKGROUND OF THE INVENTION

Systems for measuring the intra-arterial blood pressure of a patient can be subdivided into two main groups—those which invade the arterial wall to access blood pressure and those which use noninvasive techniques. Initially, the most accurate blood pressure measurements were achievable only by use of invasive methods. One such common method involved use of a fluid filled catheter inserted into a patient's artery. While invasive methods provide for accurate blood pressure measurements, the risks of infection and other complications, in many cases, outweigh the advantages of using invasive techniques.

Because of the above-mentioned risks associated with invasive methods, a noninvasive method, known as the Korotkoff method is widely used. The Korotkoff method is known as an auscultatory method because it uses, in part, the characteristic sound made as the blood flows through the artery to aid in measuring blood pressure. Although the Korotkoff method is noninvasive, it only provides a measurement of the highest pressure point (systolic) and the lowest pressure point (diastolic) along the pressure wave. While, for many purposes, systolic and diastolic pressure are sufficient, there are many applications in which it is desirable to use the entire characteristic curve of the blood pressure wave. In these applications, the Korotkoff method simply is incapable of providing satisfactory information. In addition to this limitation of the Korotkoff method, it necessitates the temporary occlusion of the artery in which blood pressure is being monitored. While arterial occlusion is not prohibitive in many applications, there are occasions where the patient's blood pressure must be monitored continuously (such as when undergoing surgery) and accordingly, the prohibiting of blood flow, even on a temporary basis, is undesirable.

Because of the above-mentioned risks associated with invasive blood pressure measurement, and the shortcomings of the Korotkoff method, extensive investigation has been conducted in the area of continuous, noninvasive blood pressure monitoring and recording. Some of these noninvasive techniques make use of tonometric principles which take advantage of the fact that as blood flows through the arterial vessel, forces are transmitted through the artery wall, through the surrounding arterial tissue and, consequently, are externally available for monitoring. Because the tonometric method of measuring blood pressure is noninvasive, it is used without the risks associated with invasive techniques. Furthermore, in addition to being more accurate than the Korotkoff method discussed above, it has the capability of reproducing the entire blood pressure wave form, as opposed to the limited systolic and diastolic pressure points provided by the Korotkoff method.

A technique for determining intra-arterial blood pressure involves the method of pressing a sensor against the tissue which overlays an artery of interest thereby flattening, or applanating, the underlying artery. This pressing is increased in intensity until a predetermined state of artery applanation is obtained. In this state, certain assumptions can be made regarding the relationship between the forces transmitted to the sensor (through the tissue overlaying the artery) and the intra-arterial blood pressure.

Thus, in view of the above discussion, it can be seen that it is desirable to provide a calibration apparatus which is effective for calibrating the response of the sensor and its associated support system. Such a calibration system should be easy to operate, and ideally, should be usable in the field. Preferably, such a calibration system should also be capable of detecting the temperature dependence of the sensor and thereby, providing the appropriate data, to the blood pressure system which uses the sensor, for compensating for the effects of temperature on the sensor head.

Thus, it is an object of this invention to provide a sensor calibration system which can be used in the field to calibrate a sensor.

It is also an object of this invention to provide a calibration system which does not necessitate dismantling the sensor from a surrounding support structure.

It is still a further object of this invention to provide a sensor calibration system which provides data to compensate for the temperature dependency of the sensor.

SUMMARY OF THE INVENTION

In light of the foregoing objects, in one aspect, the present invention provides a calibration apparatus for use in calibrating a tissue stress sensor used in a blood pressure monitoring system. The apparatus comprises a calibration head which is generally adapted to engage a support structure associated with the stress sensor. Retaining means is attached to the calibration head for retaining the head in close Proximity to the tissue stress sensor. Heating means is attached to the calibration head for heating a stress sensitive portion of the tissue stress sensor. Preferably, the calibration head includes a "C" shaped body adapted to engage the outer support structure of the tissue stress sensor and preferably the retaining means includes a thumb screw threadedly engaged through the "C" shaped body whereby rotating the thumb screw causes the thumb screw to engage the outer support structure of the tissue stress sensor thereby retaining the "C" shaped body to the outer support structure of the tissue stress sensor.

In a second aspect, the present invention provides, a calibration system for use in calibrating a sensor. The system comprises a tissue stress sensor including a sensor support structure to house the tissue stress sensor. A calibration head is provided to engage the support structure. Retaining means is used to retain the calibration head to the sensor support structure. The calibration head further includes means for heating a stress sensitive portion of the tissue stress sensor. Preferably, the sensor support structure includes a wrist strap for fastening the sensor support structure to a wrist of a wearer. Preferably, the stress sensitive portion of the tissue stress sensor further includes a continuous, stress sensitive diaphragm and a hermetically sealable chamber, wherein the chamber has a continuous wall adapted to separate an inner chamber pressure from an outer chamber pressure, wherein the continuous, stress sensitive diaphragm comprises at least a portion of the chamber wall, whereby the diaphragm is responsive to a pressure differential between the inner and outer chamber pressure.

In a third aspect, the present invention provides, a calibration system for use in calibrating a tissue stress sensor used in a blood pressure monitoring system. The tissue stress sensor is generally operative for producing an electrical output signal representative of tissue stress. The calibration system comprises means, in thermal communication with a stress sensitive portion of the tissue stress sensor, for heating the stress sensor. Also, means, are coupled to the tissue stress sensor for displacing the stress sensitive portion of the sensor. Further, a calibration means is coupled to the electrical output signal of the tissue stress sensor for detecting a response of the stress sensitive portion of the sensor to the application of a known temperature and stress. The calibration means is effective for calibrating the sensor and correcting for the effects of temperature on the data generated by the stress sensor. Preferably, the calibration means includes means for sensing the temperature of the heating means. Also, the displacing means preferably includes a vacuum pump in fluid communication with the tissue stress sensor. Preferably, the calibration means includes means for sensing a vacuum of the vacuum pump. In its most preferred embodiment, the heating means and displacing means are connected to, and controlled by the calibration means.

In a fourth aspect, the present invention provides, a calibration system for use in calibrating a blood pressure monitoring system, the blood pressure monitoring system employing a stress sensor for generating an electrical output signal representative of tissue stress. The calibration system comprises a tissue stress sensor having a stress sensitive diaphragm and a sealed chamber, the sealed chamber has a continuous wall defining an inner chamber volume and the stress sensitive diaphragm makes up a portion of the continuous wall, whereby the displaceable diaphragm is responsive to a pressure differential between the pressure within the inner chamber volume and the pressure outside of the inner chamber volume. Means is provided, in thermal communication with the stress sensitive diaphragm, for heating the diaphragm. Also, vacuum means is provided, in fluid communication with the inner volume of said sealed chamber for applying a controlled vacuum to the inner volume, whereby the diaphragm is displaced in response to the application of the vacuum. Calibration means is coupled to the electrical output signal of the tissue stress sensor for detecting the sensors response to the heating and displacing of the diaphragm and generating corrective data for use in correcting the effects of tissue stress sensor temperature on the data generated by the sensor. Preferably, the calibration means includes means for sensing the temperature of the heating means and means for sensing the vacuum of the vacuum means. In a preferred embodiment, the heating means and the vacuum means are controlled by the calibration means. Preferably, the calibration system includes a calibration head which is adapted to engage a support structure of the tissue stress sensor and wherein the calibration head is adapted to engage the heating means thereby keeping the heating means in thermal communication with the diaphragm of the sensor.

Other advantages and meritorious features of the present invention will become more fully understood from the following description of the preferred embodiments, the appended claims and the drawings, a brief description of which follows.

DETAILED DESCRIPTION OF THE PREFERRED EMBODIMENTS

Figures 1, 2, 4:
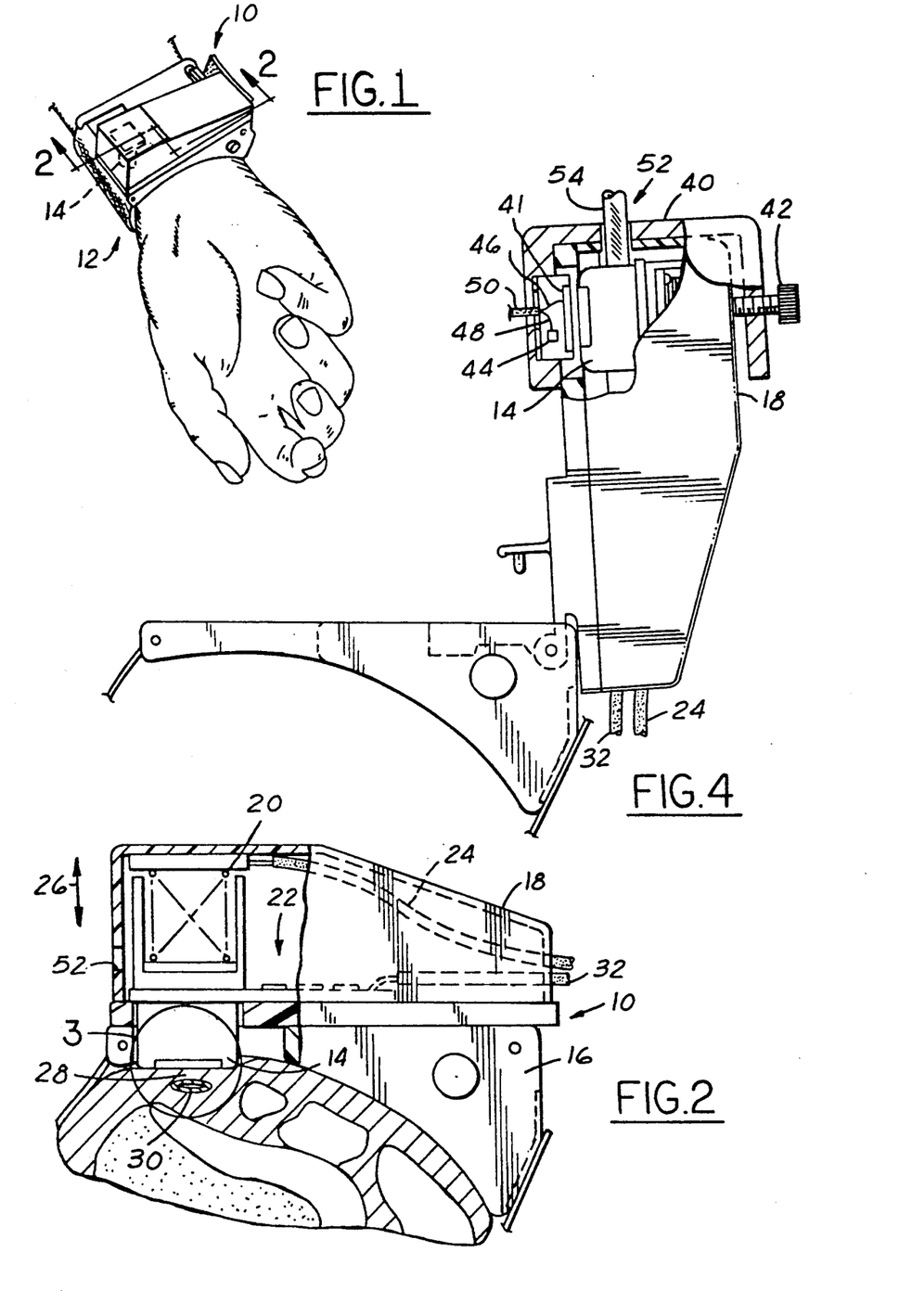
FIG. 1 is a perspective view of a wrist mount apparatus which incorporates a tissue stress sensor.
FIG. 2 is a partial cross-sectional view of a wrist mount apparatus taken substantially through lines 2—2 of FIG. 1.
FIG. 4 is a wrist mount apparatus which has the calibration apparatus of the present invention mounted to the sensor support structure.

Now referring to FIG. 1, wrist mount apparatus 10 is applied to the wrist area 12 of a user for the purpose of locating tissue stress sensor 14 in operative engagement with the tissue overlaying an artery of interest.

Now referring to FIG. 2, wrist mount apparatus 10 comprises base 16 and sensor support structure 18. Sensor support structure 18 includes tissue stress sensor 14, sensor displacement actuator 20 and sensor support electronics 22. Sensor displacement actuator 20 is controlled via link 24 and is adapted to be responsive to commands within link 24 to effect a linear movement 26. Sensor 14 is fastened to actuator 20 such that when actuator 20 effects its linear movement 26, sensor 14 is placed in operative engagement with tissue 28 overlaying an artery of interest 30. Tissue stress pulsations transmitted through tissue 28 from artery 30, are caused by intra-arterial blood pressure pulsations acting within artery 30. The diaphragm (or stress sensitive) portion 34 of sensor 14, is displaced in response to tissue contact stress loading acting upon it from tissue 28. The displacement of stress sensitive diaphragm 30, is transduced into electronic signals which are conditioned by support electronics 22 and communicated, via line 32, to the appropriate display and monitoring systems.

Figure 3:
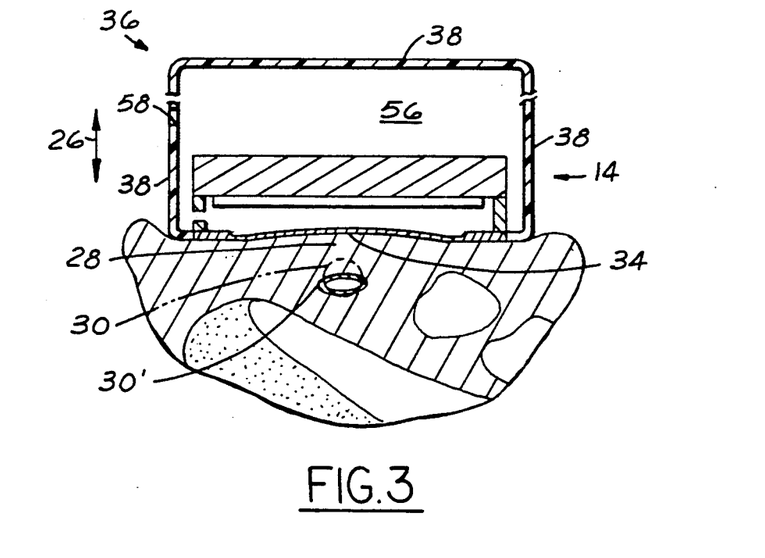
FIG. 3 is an amplified view of a tissue stress sensor and its operating environment taken substantially within encircled portion 3 of FIG. 2.

Now referring to FIG. 3, sensor 14 is comprised of continuous, stress sensitive diaphragm 34 and hermetically sealable chamber 36. Hermetically sealable chamber 36 has a continuous wall 38 adapted to separate inner chamber volume 56 from the pressure surrounding wall 38 (typically atmospheric pressure). A portion of continuous wall 38 is comprised of responsive diaphragm 34. Thus, as discussed in conjunction with FIG. 2, when sensor 14 is moved 26 into operative engagement with tissue 28 which overlies artery of interest 30, artery of interest 30' is applanated or flattened. Once the state is reached whereby artery 30 is applanated to an optimum level, the contact stress sensed by stress sensitive diaphragm 34, is well suited for use in determining the intra-arterial blood pressure of artery 30. Thus it has been demonstrated in conjunction with FIGS. 1-3 how sensor 14 is operative to engage the tissue overlying an artery of interest and is adapted to be displaced in response to intra-arterial blood pulsations. Now, in conjunction with FIGS. 4 and 5 the calibration system of the present invention will be described as it applies to calibrating sensor 14, sensor support electronics 22 and other components within a noninvasive blood pressure monitoring system.

Now referring to FIG. 4, calibration head 40 has generally a "C" shaped structure which is adapted to engage sensor support structure 18. A portion of calibration head 40 includes fastening means for thumb screw 42, which is threadedly engaged to calibration head 40 and adapted to retain calibration head 40 to sensor support structure 18. Calibration head 40 also includes heater 41 and temperature sensor 44. Although heater 41 will be used throughout the remainder of the specification to refer primarily to a device which adds thermal energy to diaphragm 34, it is also contemplated that heater 34 includes a device which is capable of removing heat energy from diaphragm 34. Cooling of diaphragm 34 may be employed in cases where it is desirable to lower the temperature of diaphragm 34 below room temperature or to simply remove heat energy from diaphragm 34 in order to quickly reduce its temperature to room temperature, etc. Consequently, it is contemplated within this disclosure, that heater 41 includes any thermal device which can operate to either heat or cool diaphragm 34. Heater 41 is preferably an electric-type heater which is provided operating current through line 46. Temperature sensor 44 can be comprised of any type of thermal detecting device such as a thermocouple, thermistor, RTD, solid state sensor or the like. The temperature sensed by sensor 44 is converted into an electric signal and sent to calibration electronics via line 48.

Both calibration head 40 is provided with opening 52 whereby vacuum tube 54 can pass therethrough and transmit a source of vacuum into hermetically sealable chamber 36 (hermetically sealable chamber 36 not shown in FIG. 4) of sensor 14.

Now referring to FIGS. 3 and 4, as was mentioned before, because responsive diaphragm 34 forms a part of continuous wall 38 of hermetically sealable chamber 36, it is responsive to a differential pressure between the pressure within chamber 36 and the air pressure surrounding hermetically sealable chamber 36. Accordingly, it can be seen that diaphragm 34 of sensor 14 can be displaced by lowering the pressure within volume 56 with respect to the air pressure outside of chamber 36 (air pressure outside of chamber 36 is typically atmospheric pressure, but this does not have to be the case). Thus, if a vacuum is placed on port 58 of chamber 36, diaphragm 34 will be displaced in the same manner in which it is displaced during actual use (when it is subjected to tissue stress). Accordingly, by applying a vacuum of known intensity to chamber 56, the fundamental relationship between diaphragm 34 deflection and the pressure necessary to cause that deflection can be established. It is important to note, that in this respect, the design of sensor 14 plays an important role in the calibration system of the present invention. Specifically, by designing hermetically sealable chamber 36 so as to make responsive diaphragm 34 a part of continuous wall 38, a calibrated vacuum can be used to, in essence, simulate the application of a calibrated pressure across responsive diaphragm 34 of sensor 14. This is seen as a substantial advantage of the disclosed calibration system, inasmuch as the application of a vacuum to an open faced sensor of the type used in tonometry, is generally considered to be much easier to administer than the alternative which would be to attempt to present a calibrated pressure across the external face of diaphragm 34. Two obvious disadvantages with using the external pressure approach include providing a simple and effective way to seal the pressure source against the external face of diaphragm 34 and gaining necessary access to sensor 14 to apply the calibrated pressure without necessitating removing sensor 14 from its support structure 18. Also, when using the external pressure approach to seal the pressure source against the external face of diaphragm 34, care must be taken to exert sufficient force in order to seal the pressure source against the face of the diaphragm while preventing the application of excessive force against the diaphragm stress structure which tends to stress diaphragm 34 thereby introducing measurement errors.

Figure 5:
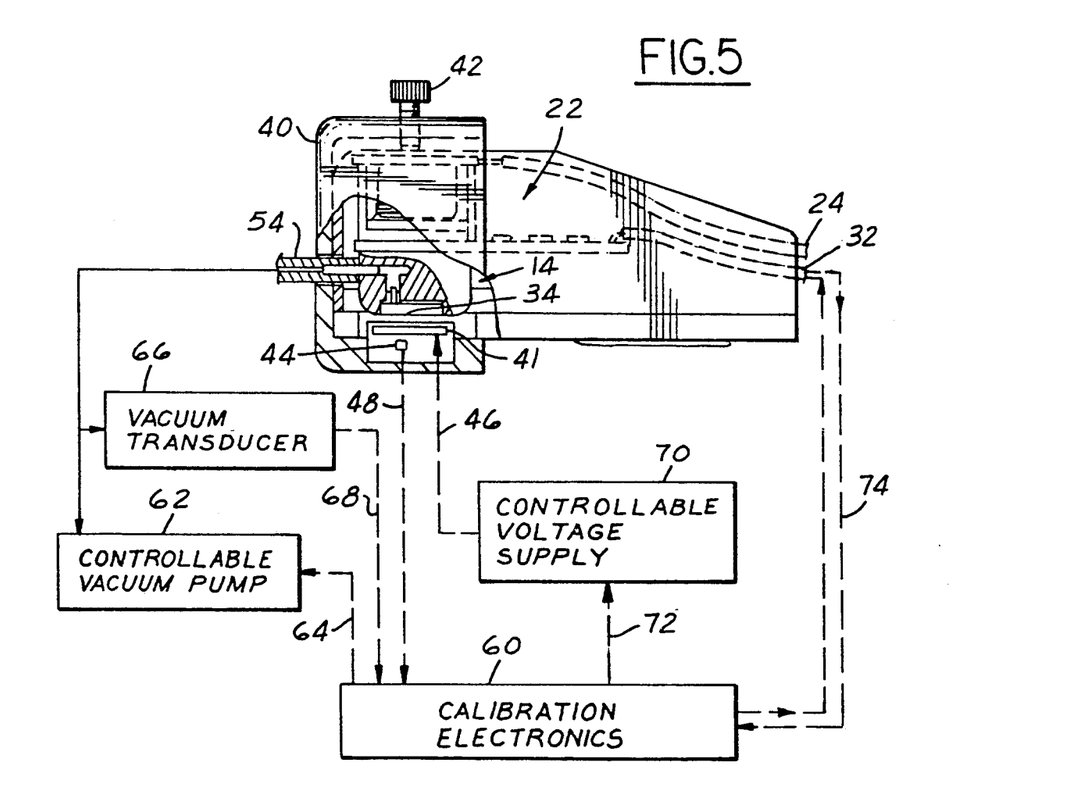
FIG. 5 is a diagrammatic depiction of the calibration system of the present invention.

Now referring io FIG. 5, heater 41 is mounted within "C" shaped calibration head 40 such that it is in close proximity to, but does not directly contact, responsive diaphragm 34. In this manner, heater 41 is effective for heating diaphragm 34 but does not transmit any contaminants thereto, nor does it expose diaphragm 34 to damage caused by bumping heater 41 against diaphragm 34. Preferably, heater 41 operates to uniformly heat the entire stress sensitive (or diaphragm) portion 34 of stress sensor 14. This uniform heating is preferably accomplished by extending heater 41 along the full length of diaphragm 34. Temperature sensor 44 is placed in close proximity to heater 41 thereby sensing the approximate temperature of diaphragm 34 and sending the sensed temperature along line 48 to calibration electronics 60. Vacuum tube 54 fluidly couples vacuum from controllable vacuum pump 62 into inner chamber 56. Accordingly, as has been discussed in conjunction with FIG. 3, a vacuum applied by pump 62 is effective for displacing diaphragm 34. Pump 62 is controlled by calibration electronics via line 64. Accordingly, voltage signals sent out from calibration electronics 60 to pump 62 can control the amount of vacuum applied to diaphragm 34 thereby controlling its displacement. Vacuum transducer 66 senses the vacuum in tube 54 and transduces that vacuum into an electric signal and presents it to calibration electronics 60 via line 68. Now the calibration system set out in FIG. 5 will be used to explain the general procedure for calibrating transducer 14 and support electronics 22.

Calibration electronics 60 first sends out a signal to controllable voltage supply 70 to generally heat diaphragm 34 to a predetermined temperature. This temperature is preferably a temperature within the temperature range experienced by diaphragm 34 during actual operating conditions. Sensor 44 is responsive to the actual temperature of heater 41 and calibration electronics 60 can constantly monitor and control the diaphragm temperature and use this temperature information in generating corrective data for use in correcting the effects of tissue stress sensor temperature on the data generated by the sensor. After diaphragm 34 has stabilized at a predetermined temperature, various vacuum settings can be applied to diaphragm 34 thereby giving rise to various degrees of diaphragm deflection. Diaphragm deflection is sensed by sensing electronics (sensing electronics not shown) and further conditioned by support electronics 22. Support electronics 22 encode the deflection of diaphragm 34 into electronic signals and pass them along to calibration electronics 60 along line 74. Thus it can be seen that the calibration system set out in FIG. 5 is effective for measuring the displacement of diaphragm 34 in response to a known vacuum (which can be used to calculate the equivalent pressure across diaphragm 34) and a known temperature. Thus, by setting various vacuum and temperature points and monitoring the electrical signals produced on line 74, a collection of characteristic data can be generated to generally define the calibration characteristics of diaphragm 34, sensor support electronics 22 and any other system which intervenes between calibration and electronics and diaphragm 34. Thus, it can be easily seen that the function accomplished by calibration electronics 60 can be implemented by using either hardware or software techniques. If software techniques are utilized, a single system may be designed to function both in a calibration mode and an operation mode. Thus, the same system would be used for calibrating the sensor and monitoring its output during actual use conditions. The following description sets out a preferred methodology for calibrating the sensor system set out in FIG. 5.

The tonometer stress contact sensor of the present invention generates a plurality of electrical signals which are each a function of local diaphragm 34 deflection and local diaphragm 34 temperature. First consider the simplest model of this sensor neglecting the contribution of temperature, and assume a linear relationship between output current and stress.

If p=the displayed value of pressure in mmHg, then $$p = SLOPE \cdot x + OFFSET$$

where SLOPE and OFFSET are calibration constants, and x is an electrical signal assumed to be a linear function of pressure.

For this model, the two calibration constants are calculated in software by substituting the desired values of p and the measured values of x for the following two known conditions:

0 mmHg applied to sensor, 120 mmHg applied to sensor.

However, the contribution of temperature to the sensor function is significant, and cannot be neglected. The simplest model of the function of pressure and temperature assumes that the OFFSET term is a linear function of temperature, and that the SLOPE term is a constant independent of temperature.

If we let d=the displayed value of pressure in mmHg, then, $$d = XSLOPE \cdot x + (RSLOPE \cdot r + OFFSET)$$

where XSLOPE, RSLOPE, and OFFSET are calibration constants, x is assumed to be a linear function of pressure and temperature and r is assumed to be a linear function of temperature.

The r input is derived from the reference sensor previously mentioned which has an opto electronic structure identical to that which generates the x input, except that it is not modulated by pressure. It is located such that it is in the same environment, and consequently, at the same temperature as the x opto electronics.

For this model, the three calibration constants are calculated in software by inserting the desired values of d and the measured values of x and r for the following three known conditions:

0 mmHg applied to sensor at temperature 1,
120 mmHg applied to sensor at temperature 1,
0 mmHg applied to sensor at temperature 2.

However, the effect of temperature on the SLOPE coefficient is also significant, and cannot be neglected. A model which also accounts for this effect, assuming it is linear, is constructed as follows:

$$d = [RXSLOPE \cdot r + XOFFSET] \cdot x + [RSLOPE \cdot r + OFFSET]$$

where d is the displayed value of pressure in mmHg, RXSLOPE, XOFFSET, RSLOPE, and OFFSET are calibration constants, x is assumed to be a linear function of pressure and temperature, and r is assumed to be a linear function of temperature.

For this model, the four calibration constants are calculated in software by inserting the desired values of d and the measured values of x and r for the following four known conditions:

0 mmHg applied to sensor at temperature 1, (p1, t1)
120 mmHg applied to sensor at temperature 1, (p2, t1)
0 mmHg applied to sensor at temperature 2, (p1, t2)
120 mmHg applied to sensor at temperature 2, (p2, t2).

A method of automatically performing these four calibrations in computer software, so that there is no interaction between conditions, i.e., calibration of any condition does not require recalibration of any previously calibrated condition, is derived as follows:

0 mmHz. temperature 1 cal:
From model, $$d = [RXSLOPE \cdot r + XOFFSET] \cdot x + [RSLOPE \cdot r + OFFSET] \quad (1)$$

and, since we expect to display 0 mmHg at p1 and t1, $$0 = [RXSLOPE \cdot r(t1) + XOFFSET] \cdot x(p1,t1) + [RSLOPE \cdot r(t1) + OFFSET] \quad (2)$$

Solving (2).

$$OFFSET = -[RXSLOPE \cdot r(t1) + XOFFSET] \cdot x(p1,t1) - RSLOPE \cdot r(t1) \quad (3)$$

The input values are saved as:

$R11 = r(t1)$ $X11 = x(p1,t1)$ where
p1 = 0 mmHg applied pressure, and
t1 = temperature 1.
Substituting the p2 and t1 conditions into (1), $$120 = [RXSLOPE \cdot r(t1) + XOFFSET] \cdot x(p2,t1) + [RSLOPE \cdot r(t1) + OFFSET] \quad (4)$$

Subtracting (4)−(2), $$120 = [RXSLOPE \cdot r(t1) + XOFFSET] \cdot [x(p2,t1) - x(p1,t1)] \quad (5)$$

$$120 = [RXSLOPE \cdot r(t1) + XOFFSET] \cdot [x(p2,t1) - X11] \quad (6)$$

Solving (6), $$XOFFSET = 120 \div [x(p2,t1) - X11] - RXSLOPE \cdot r(t1) \quad (7)$$

Readjusting OFFSET from (3), $$OFFSET = -[RXSLOPE \cdot R11 + XOFFSET]X11 - RSLOPE \cdot R11 \quad (8)$$

The input values are saved as:

$$R21 = r(t1)$$

$$X21 = x(p2,t1)$$

where
p2 = 120 mmHg applied pressure, and
t1 = temperature 1.
0 mmHz. temperature 2 cal:
Substituting the p1 and t2 conditions into (1), $$0 = [RXSLOPE \cdot r(t2) + XOFFSET] \cdot x(p1,t) + [RSLOPE \cdot r(t2) + OFFSET] \quad (9)$$

Subtracting (9) − (2)

$$0 = [RXSLOPE \cdot [r(t2) \cdot x(p1,t2) - r(t1) \cdot x(p1,t1)] + XOFFSET \cdot [x(p1,t2) - x(p1,t1)] + RSLOPE \cdot [r(t2) - r(t1)] \quad (10)$$

Solving (10), $$RSLOPE = -\{RXSLOPE \cdot [r(t2) \cdot x(p1,t2) - R11 \cdot X11] + XOFFSET \cdot [x(p1,t2) - x11]\} \div \{r(t2) - R11\} \quad (11)$$

Readjusting OFFSET from (3), $$OFFSET = -[RXSLOPE \cdot R11 + XOFFSET] \cdot X11 - RSLOPE \cdot R11 \quad (12)$$

The input values are saved as:

$$R12 = r(t2)$$

$$X12 = x(p1,t2)$$

where
p1 = 0 mmHg applied pressure. and
t2 = temperature 2.
120 mmHg, temperature 2 cal:
Substituting the p2 and t2 conditions into (1).

$$120 = [RXSLOPE \cdot r(t2) + XOFFSET] \cdot x(p2,t2) + [RSLOPE \cdot r(t2) + OFFSET] \quad (13)$$

Subtracting (13) − (9), $$120 = [RXSLOPE \cdot r(t2) + XOFFSET] \cdot [x(p2,t2) - x(p1,t2)] = [RXSLOPE \cdot r(t2) + XOFFSET] \cdot [x(p2,t2) - X12] \quad (14)$$

$$RXSLOPE \cdot r(t2) + XOFFSET = 120 \div [x(p2,t2) - X12] \quad (15)$$

From (7) and (8), $$XOFFSET = [120 \div \{x21 - x11\}] - RXSLOPE \cdot R21 \quad (16)$$

Substituting (16) into (15), $$RXSLOPE \cdot [r(t2) - R21] = [120 \div \{x(p2,t2) - X12\}] - [120 \div \{x21 - x11\}]$$

$$RXSLOPE = [120 \div \{r(t2) - R21\}] \cdot [[1 \div \{x(p2,t2) - x12\}] - [1 \div \{x21 - x11\}]] \quad (17)$$

Readjust XOFFSET by computing from (16) with the new value of RXSLOPE inserted.

Readjust RSLOPE from (11) with the new values of RXSLOPE and XOFFSET inserted.

Readjust OFFSET from (12) with the new values of RXSLOPE, XOFFSET, and RSLOPE inserted.

The function of the calibration points, in the order discussed above, is as follows:

| | |
|---|---|
| Point 1 | Set pressure offset (zero point). |
| Point 2 | Set pressure slope (gain). |
| Point 3 | Set offset (zero point) compensation. |
| Point 4 | Set slope (gain) compensation. |

As can be seen from the above method, there is no interaction between the calibration points. The points may be calibrated in any order, and not all points need be calibrated. For example, if operation will only occur at temperature 1, only the first two points need be calibrated. If only the offset needs to be corrected, the first point calibration is sufficient. If only the full scale point at temperature 1 needs correction, only the second point need be calibrated.

The foregoing detailed description shows that the preferred embodiments of the present invention are well suited to fulfill the objects of the invention. It is recognized that those skilled in the art may make various modifications or additions to the preferred embodiments chosen here to illustrate the present invention, without departing from the spirit of the present invention. Accordingly, it is to be understood, that the subject matter sought to be afforded protection hereby should be deemed to extend to the subject matter defined in the appended claims, including all fair equivalents thereof.

We claim:

1. A calibration apparatus for use in calibrating a tissue stress sensor used in a blood pressure monitoring system, said apparatus comprising:
    a calibration head,
        means, attached to said calibration head, for retaining said calibration head in close proximity to said tissue stress sensor, and
        means, attached to said calibration head, for heating said tissue stress sensor.

2. The calibration apparatus of claim 1, wherein said calibration head generally includes a "C" shaped body adapted to engage a portion of an outer support structure surrounding said tissue stress sensor.

3. The calibration head of claim 2, wherein said retaining means includes a thumb screw threadedly engaged through said "C" shaped body, whereby rotating said thumb screw causes said thumb screw to engage said outer support structure of said tissue stress sensor thereby retaining said "C" shaped body to said outer support structure of said tissue stress sensor.

4. A calibration system for use in calibrating a sensor, comprising:
    a tissue stress sensor including a sensor support structure to house said tissue stress sensor,
    a calibration head, adapted to engage said support structure, means for retaining said calibration head to said sensor support structure, and means, attached to said calibration head, for heating said tissue stress sensor.

5. The calibration system of claim 4, wherein said sensor support structure includes a wrist strap for fastening said sensor support structure to a wrist of a wearer.

6. The calibration system of claim 5, wherein said calibration head generally includes a "C" shaped body adapted to engage an outer surface portion of said support structure.

7. The calibration system of claim 6, wherein said retaining means includes a thumb screw threadedly engaged to said "C" shaped body, whereby rotating said thumb screw causes said thumb screw to engage said sensor support structure thereby retaining said "C" shaped body to said sensor support structure.

8. The calibration system of claim 4, wherein said tissue stress sensor further includes a continuous, stress sensitive diaphragm and a continuous wall defining a hermetically sealable chamber, said continuous wall adapted to separate an inner chamber pressure from a pressure outside said chamber, wherein said continuous, stress sensitive diaphragm comprises at least a portion of said continuous wall, whereby said diaphragm is responsive to a pressure differential between said inner chamber pressure and said pressure outside said chamber.

9. A calibration system for use in calibrating a tissue stress sensor used in a blood pressure monitoring system, said sensor of the type having a stress sensitive portion for sensing tissue stress, said tissue stress sensor generating an electrical output signal representative of tissue stress, comprising:

means, adapted to be in thermal communication with said stress sensitive portion of said tissue stress sensor, for heating said stress sensitive portion of said tissue stress sensor, means, adapted to be coupled to said tissue stress sensor, for displacing said stress sensitive portion of said tissue stress sensor, calibrating means, adapted to be coupled to said electrical output signal of said tissue stress sensor, for detecting a response of said stress sensitive portion of said sensor to said heating and displacing of said stress sensitive portion of said tissue stress sensor, and correcting the effects of temperature on said electrical output signal of said tissue stress sensor.

10. The calibration system of claim 9, wherein said calibration means further includes means for sensing the temperature of said heating means.

11. The calibration system of claim 9, wherein said means for displacing includes a vacuum pump adapted to be in fluid communication with said stress sensitive portion of said tissue stress sensor.

12. The calibration system of claim 11, wherein said calibration means includes means for sensing a vacuum of said vacuum pump.

13. The calibration system of claim 9, wherein said heating means and said displacing means are connected to, and controlled by, said calibration means.

14. The calibration system of claim 13, wherein said heating means is adapted to heat said stress sensitive portion of said tissue stress sensor in response to a first control signal from said calibration means, and wherein displacing means is adapted to displace said stress sensitive portion of said tissue stress sensor in response to a second control signal from said calibration means.

15. A calibration system for use in calibrating a blood pressure monitoring system, comprising:

a tissue stress sensor having a stress sensitive diaphragm and a continuous wall defining a sealable chamber; said continuous wall defining an inner chamber volume and wherein said stress sensitive diaphragm comprises a portion of said continuous wall, whereby said stress sensitive diaphragm is responsive to a pressure differential between the pressure of said inner chamber volume and a pressure outside of the inner chamber volume, means, in thermal communication with said stress sensitive diaphragm, for heating said stress sensitive diaphragm, vacuum means, fluidly coupled to said inner volume of said sealable chamber, for applying a controlled vacuum to said inner chamber volume of said sealable chamber, whereby said stress sensitive diaphragm is displaced in response to said application of said vacuum, and calibration means, coupled to an electrical output signal of said tissue stress sensor, for detecting said sensor's response to said heating and displacing of said stress sensitive diaphragm, and generating corrective data for use in correcting the effects of tissue stress sensor temperature on the electrical output signal of said tissue stress sensor.

16. The calibration system of claim 15, wherein said calibration means further includes means for sensing the temperature of said heating means.

17. The calibration system of claim 15, wherein said vacuum means includes a vacuum pump.

18. The calibration system of claim 17, wherein said calibration means includes means for sensing a vacuum of said vacuum pump.

19. The calibration system of claim 15, wherein said heating means and said vacuum means are connected to, and controlled by, said calibration means.

20. The calibration system of claim 19, wherein said heating means is adapted to heat said stress sensitive diaphragm in response to a first control signal from said calibration means, and wherein said vacuum means is adapted to displace said stress sensitive diaphragm in response to a second control signal from said calibration means.

21. The calibration system of claim 15, wherein said tissue stress sensor includes a sensor support structure which includes a wrist strap for fastening said sensor support structure to a wrist of a wearer.

22. The calibration system of claim 21, further including a calibration head, adapted to engage said support structure, and wherein said calibration head is adapted to engage said heating means thereby keeping said heating means in thermal communication with said stress sensitive diaphragm, and wherein said calibration head generally includes a "C" shaped body adapted to engage an outer surface portion of said sensor support structure.

23. The calibration system of claim 22, wherein said calibration head "C" shaped body includes a thumb screw threadedly engaged to said "C" shaped body, whereby rotating said thumb screw causes said thumb screw to engage said sensor support structure thereby retaining said "C" shaped body to said sensor support structure.

24. A tissue stress sensor of the type used to non-invasively determine intra-arterial blood pressure, said tissue stress sensor comprising:
- a continuous stress sensitive diaphragm including means for placing said diaphragm in direct communication with tissue overlying an artery of interest,
- a continuous wall,
- a vacuum port through said continuous wall,
- wherein said continuous stress sensitive diaphragm comprises a portion of said continuous wall, and
- wherein said continuous wall and said continuous stress sensitive diaphragm form a sealable air tight chamber,
- whereby said tissue stress sensor is used as a stress sensor and said continuous diaphragm is responsive to stresses imparted to it from said tissue overlying an artery of interest, and whereby when said tissue stress sensor is calibrated, a calibrated vacuum is applied to said vacuum port thereby lowering the pressure within said air tight chamber, whereby said continuous diaphragm responds to a pressure differential established between the sealable air tight chamber and a pressure upon an outer surface of said continuous diaphragm, said response of said continuous diaphragm to said pressure differential being in part due to the magnitude of said calibrated vacuum, whereby said application of said calibrated vacuum to said vacuum port enables said tissue stress sensor to be calibrated.

25. The tissue stress sensor of claim 24, further including calibrated vacuum means connected to said vacuum port for lowering the pressure within said air tight chamber.

26. The tissue stress sensor of claim 25, wherien said calibrated vacuum means includes a vacuum source and a vacuum tube connected between said vacuum source and said vacuum port, wherein said vacuum tube includes an end portion adapted to engage a seal along an inne surface of said vacuum port thereby forming an air tight seal between said port and said vacuum tube.

UNITED STATES PATENT AND TRADEMARK OFFICE
CERTIFICATE OF CORRECTION

PATENT NO. : 5,195,522
DATED : March 23, 1993
INVENTOR(S) : Pytel, et al.

It is certified that error appears in the above-identified patent and that said Letters Patent is hereby corrected as shown below:

Column 14, line 14, "wherien" should read --wherein--.

Column 14, line 19, "inne" should read --inner--.

Signed and Sealed this

Twenty-first Day of March, 1995

Attest:

BRUCE LEHMAN

*Attesting Officer*  *Commissioner of Patents and Trademarks*